US00PP18311P2

(12) United States Plant Patent

Korlipara

(10) Patent No.: US PP18,311 P2

(45) Date of Patent: Dec. 11, 2007

(54) *VERBASCUM* PLANT NAMED 'GOLD NUGGET'

(50) Latin Name: ***Verbascum* hybrid** ((*V. phoeniceum*×*dumulosum*)×*V. bombyciferum*, Arctic Summer)
Varietal Denomination: Gold Nugget

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 22 days.

(21) Appl. No.: 11/444,888

(22) Filed: May 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman

(57) ABSTRACT

A new and distinct *Verbascum* plant characterized by numerous yellow flowers with red eyes, on upright, branching flowering stems, and excellent vigor. The foliage is colored a soft silver gray. The habit is compact.

1 Drawing Sheet

Botanical classification: *Verbascum* hybrid ((*V. phoeniceum*×*dumulosum*)×*V. bombyciferum* 'Arctic Summer').

Variety denomination: 'Gold Nugget'.

The present invention relates to a new and distinct cultivar of *Verbascum* hybrid, and given the cultivar name 'Gold Nugget'. *Verbascum* is in the family *Scrophulariaceae.*

This new cultivar originated as a controlled cross in a cultivated area between *Verbascum* 'Jackie' (an unpatented plant) as the seed parent and *Verbascum bombyciferum* 'Arctic Summer' (an unpatented plant) as the pollen parent. *Verbascum* 'Jackie' is a cross between *Verbascum phoeniceum* and *Verbascum dumulosum.*

This new *Verbascum* hybrid is unique in its large gold colored flowers with bright red eyes combined with its short, multiple flowering stems and silvery leaves.

This plant is characterized by the following:

1. Large yellow flowers with bright red eyes.
2. Numerous upright, branching flowering stems.
3. Large, soft silver gray leaves.
4. Short flowering stems.
5. Small habit.
6. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without change in the genotype of the plant.

BRIEF DESCRIPTION OF THE DRAWING

The photograph shows the whole plant of a one year old *Verbascum* 'Gold Nugget' grown in the ground in the trail field in bloom in summer.

DETAILED PLANT DESCRIPTION

The following is a detailed description of the new *Verbascum* selection based on observations of one-year-old specimens grown in the ground in full sun under typical outdoor conditions in Canby, Oreg. Canby in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 6–9.
*Size.*—15 cm tall and 26 cm wide, not including inflorescence.
*Vigor.*—Excellent.
*Roots.*—Fibrous, with many downward growing and few laterals, ivory in color, Yellow White 158D. Roots develop slowly from cuttings from the crown.

Leaf:

*Type.*—Simple.
*Arrangement.*—Basal.
*Shape.*—Ovate.
*Blade size.*—Grows to 16 cm long and 8.5 cm wide.
*Venation.*—Pinnate.
*Margins.*—Crenate.
*Apex.*—Acute.
*Base.*—Cuneate.
*Texture.*—Leathery, fuzzy.
*Surface.*Stellate pubescent on both sides.
*Petiole.*—Length — grows to 5 cm. Width — grows to 6 mm. Surface — densely stellate pubescent. Color —Yellow Green 145C.
*Leaf color.*—Top side — between Yellow Green 147A and Greyed Green 191A with lighter main vein, Yellow Green 145C. Bottom side — Yellow Green 147B with lighter netted veins Yellow Green 145C.

Inflorescence:

*Type.*—Panicle.

*Total panicle size.*—14 cm wide and 30 cm high (where flowers are).

*Number of panicles per plant.*—5.

*Cauline leaves.*—Usually 10 in 3.5 cm internodes, lower leaves petiolate, 3 cm to 14 cm long and 2 to 4.7 cm wide (including petioles), ovate, with tips acute, margins crenate, densely stellate pubescent, color the same as the basal leaves.

*Flower number.*—Count of 100 to 170 flowers on one panicle.

*Peduncle.*—Height — Grows to 52 cm. Diameter — 10 mm near base. Surface — Densely stellate pubescent. Color — Yellow Green 147C.

*Pedicel.*—Length — Grows to 8 mm. Surface — Densely stellate pubescent. Color — Yellow Green 145C.

*Bloom time.*—May through August in Canby, Oreg.

Flower Bud:

*Size.*—12 mm wide and 11 mm deep.

*Description.*—Pentagonal cushion.

*Surface.*—Stellate pubescent.

*Color.*—Greyed Orange 165B.

Flower:

*Type.*—Perfect, complete, irregular.

*Shape.*—Rotate, irregular, short tubular.

*Size.*—4 cm wide and 12 mm deep including stamens.

*Color.*—Yellow 9B on both sides, with the center of the inside of the corolla eyed, Greyed Purple 183B.

*Corolla description.*—5 overlapping lobes, margins entire, apex obtuse, glabrous on top side, glandular on bottom side, 4 cm wide and 7 mm deep, slightly cupped.

*Calyx description.*—5 lobes, 9 mm wide and 6 mm deep, densely stellate pubescent and glandular on back side, glandular inside, Yellow Green 147B on both sides.

*Stamen.*—5, the three top stamen are 11 mm long, the lower two are 12 mm long, all are heavily bearded from the bottom with Purple 79B, the bottom three are bearded with White 155B at the top of the filaments, the top of the top two filaments is Orange 22A and not bearded; anthers are kidney shaped and Orange 22A; pollen is Orange 25A.

*Pistil.*—17 mm long, ovary is 2.5 mm long and Green 138D, style is 13 mm long and Yellow Green 147C to 147D, stigma is Yellow Green 147A.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

Compared to *Verbascum bombyciferum* 'Arctic Summer' (unpatented), the pollen parent, *Verbascum* 'Gold Nugget' has darker flowers, smaller greener leaves, much more branching, and is much shorter.

Compared to *Verbascum* 'Jackie' (unpatented), the seed parent, *Verbascum* 'Gold Nugget' has flowers that are yellow with red eyes rather than pale peach and leaves that are silver gray rather than green.

'GOLD NUGGET' has yellow flowers (RHS 9B) with bright red eyes (RHS 183B) and the top of the leaves is silver-gray (between RHS 147A and 191A). In contrast, 'LEMON SORBET' has yellow flowers (RHS 14A, tinged with RHS 22A) and the top of the leaves is green (RHS 146B).

I claim:

1. A new and distinct *Verbascum* plant as herein illustrated and described.

* * * * *

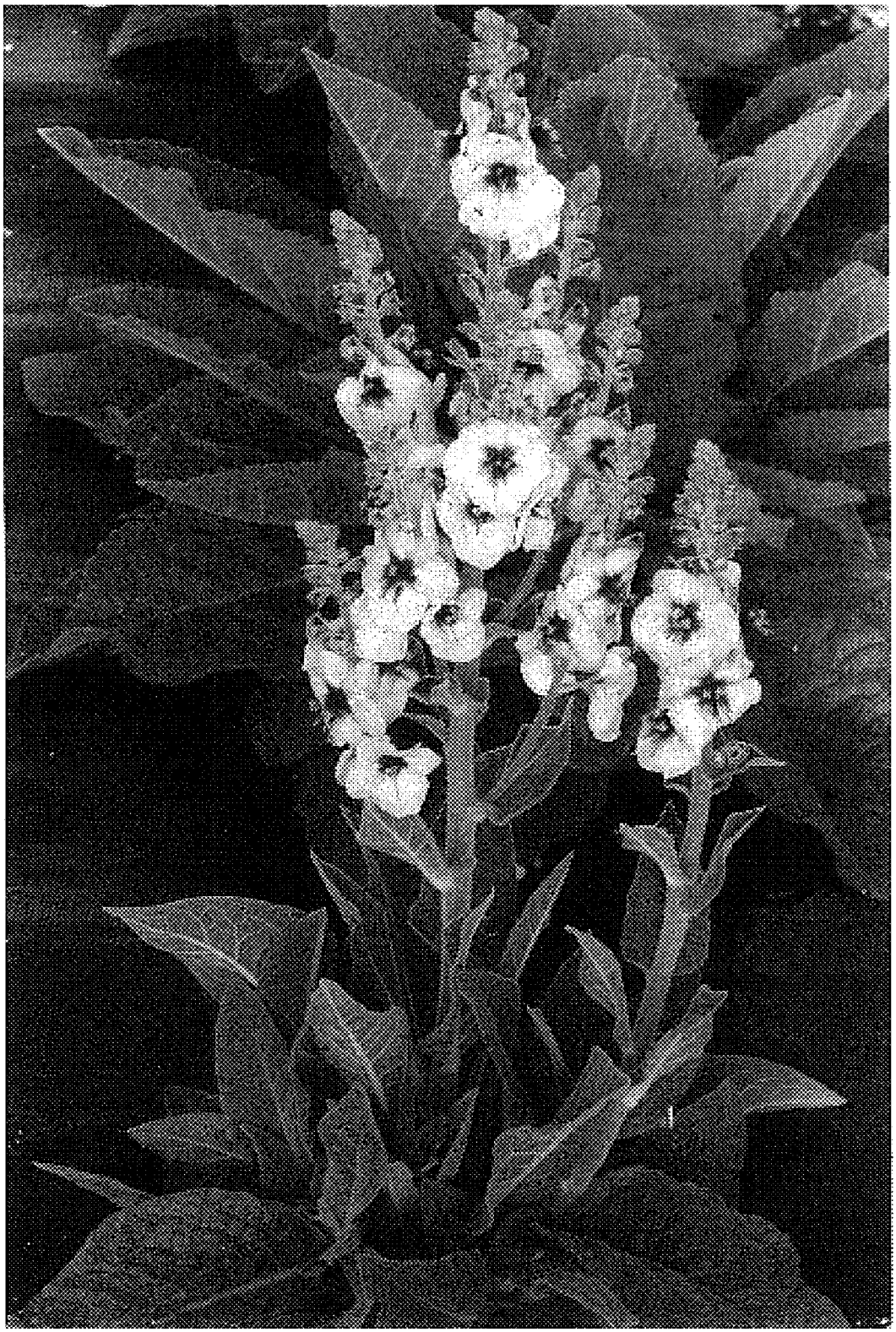

UNITED STATES PATENT AND TRADEMARK OFFICE

CERTIFICATE OF CORRECTION

PATENT NO. : PP 18,311 P2
APPLICATION NO. : 11/444888
DATED : December 11, 2007
INVENTOR(S) : Harini Korlipara It is certified that error appears in the above-identified patent and that said Letters Patent is hereby corrected as shown below:

Column 1, line 39, "trail" should be --trial--.

Column 2, line 6, "Canby in Zone 8" should be --Canby is Zone 8--.

Column 2, line 33, "*Surface*.Stellate" should be --*Surface* - densely stellate--.

Signed and Sealed this

Eighth Day of July, 2008

JON W. DUDAS
*Director of the United States Patent and Trademark Office*